United States Patent [19]

Franckowiak et al.

[11] Patent Number: 4,898,865
[45] Date of Patent: Feb. 6, 1990

[54] [4-(6-OXO-1,4,5,6-TETRAHYDRO-3-PYRIDAZINYL) ANILINO HEXYL 1,4-DIHYDRO-2,6 DI METHYL 5 NITRO 4 ARYL PYRIDINE 3-CARBOXYLATES

[75] Inventors: Gerhard Franckowiak; Martin Bechem, both of Wuppertal; Michael Kayser, Leverkusen; Rainer Gross, Wuppertal; Matthias Schramm, Cologne; Friedel Seuter; Elisabeth Perzborn, both of Wuppertal, all of Fed. Rep. of Germany; Günther Thomas, Arese, Italy

[73] Assignee: Bayer Aktiengesellschaft, Leverkusen, Fed. Rep. of Germany

[21] Appl. No.: 218,759

[22] Filed: Jul. 13, 1988

[30] Foreign Application Priority Data

Jul. 28, 1987 [DE] Fed. Rep. of Germany ....... 3724909

[51] Int. Cl.⁴ .................. A61K 31/495; C07D 403/14
[52] U.S. Cl. .................................... 514/252; 544/238; 544/239
[58] Field of Search ......................... 544/238; 514/252

[56] References Cited

U.S. PATENT DOCUMENTS

| 3,996,234 | 12/1976 | Bossert et al. | 546/321 |
| 4,248,873 | 3/1981 | Bossert et al. | 544/238 |
| 4,578,395 | 3/1986 | Yamaguchi | 546/321 |
| 4,618,607 | 10/1986 | Araki et al. | 514/252 |
| 4,622,332 | 11/1986 | Wehinger | 544/238 |
| 4,652,573 | 3/1987 | Minaskanlan | 544/238 |
| 4,661,484 | 4/1987 | Okushima | 514/242 |
| 4,686,229 | 8/1987 | Rosentreter | 544/238 |
| 4,707,479 | 11/1987 | Meyer et al. | 544/238 |
| 4,731,370 | 3/1988 | Watanabe | 514/252 |

FOREIGN PATENT DOCUMENTS 0071819 2/1983 European Pat. Off. .
0173204 3/1986 European Pat. Off. .
0174654 3/1986 European Pat. Off. .
0185964 7/1986 European Pat. Off. .

Primary Examiner—Donald G. Daus
Attorney, Agent, or Firm—Sprung Horn Kramer & Woods

[57] ABSTRACT

Circulation active nitrodihydropyridines of the formula

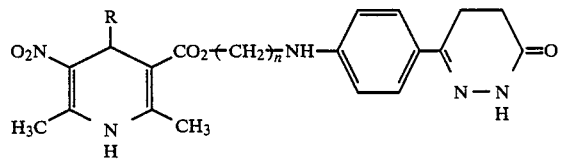

in which
R represents aryl which has 6 to 12 carbon atoms and can be substituted up to 4 times, identically or differently, by halogen, nitro, cyano, alkyl, alkoxy, alkylthio, in each case having up to 6 carbon atoms, trifluoromethyl, trifluoromethoxy, difluoromethoxy, trifluoromethylthio, difluoromethylenedioxy, trifluoroethylenedioxy or tetrafluoroethylenedioxy or by benzyl, benzyloxy or benzylthio, each of which is optionally substituted by halogen, nitro, cyano, trifuoromethyl, alkyl having up to 4 carbon atoms or alkoxy having up to 4 carbon atoms, or represents a heterocycle which is optionally substituted by halogen, phenyl or alkyl having up to 4 carbon atoms and is from the group consisting of pyrryl, thienyl, furyl, pyrazolyl, imidazolyl, oxazolyl, thiazolyl, pyridyl, pyrimidyl, pyridazinyl, quinolyl, benzoxadiazolyl, chromenyl or thiochromenyl, and
n represents a number from 1 to 12,
and physiologically acceptable salts thereof.

10 Claims, No Drawings

[4-(6-OXO-1,4,5,6-TETRAHYDRO-3-PYRIDAZI-NYL) ANILINO HEXYL 1,4-DIHYDRO-2,6 DI METHYL 5 NITRO 4 ARYL PYRIDINE 3-CARBOXYLATES

The invention relates to new substituted nitrodihydropyridines, to several processes for their preparation, and to their use in medicaments, in particular for combating circulatory diseases and thromboses.

The present invention relates to new substituted nitrodihydropyridines of the general formula (I)

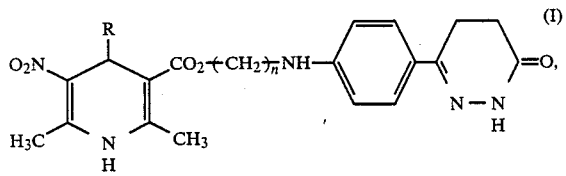

in which
R represents aryl which has 6 to 12 carbon atoms and can be substituted up to 4 times, identically or differently, by halogen, nitro, cyano, alkyl, alkoxy, alkylthio, in each case having up to 6 carbon atoms, trifluoromethyl, trifluoromethoxy, difluoromethoxy, trifluoromethylthio, difluoromethylenedioxy, trifluoroethylenedioxy or tetrafluoroethylenedioxy or by benzyl, benzyloxy or benzylthio, each of which is optionally substituted by halogen, nitro, cyano, trifluoromethyl, alkyl having up to 4 carbon atoms or alkoxy having up to 4 carbon atoms, or represents a heterocycle which is optionally substituted by halogen, phenyl or alkyl having up to 4 carbon atoms and is from the series comprising pyrryl, thienyl, furyl, pyrazolyl, imidazolyl, oxazolyl, thiazolyl, pyridyl, pyrimidyl, pyridazinyl, quinolyl, benzoxadiazolyl, chromenyl or thiochromenyl, and
n represents a number 1 to 12,
and to their physiologically acceptable salts.

Preferred compounds of the general formula (I) are those in which
R represents phenyl or naphthyl, each of which can be substituted up to 3 times, identically or differently, by fluorine, chlorine, bromine, nitro, cyano, alkyl, alkoxy, alkylthio, each having up to 4 carbon atoms, trifluoromethyl, trifluoromethoxy or trifluoromethylthio, or benzyloxy or benzylthio, each of which is optionally substituted by nitro, fluorine, chlorine, bromine, trifluoromethyl, methyl or methoxy, or represents a heterocycle which is optionally substituted by methyl, fluorine, chlorine, bromine or phenyl and is from the series comprising thienyl, furyl, pyridyl, pyrimidyl, quinolyl, benzoxadiazolyl or thiochromenyl, and
n represents a number 1 to 10,
and their physiologically acceptable salts.

Particularly preferred compounds of the general formula (I) are those in which
R represents phenyl which can be substituted up to twice, identically or differently, by fluorine, chlorine, nitro, cyano, alkyl, alkoxy, each having up to 4 carbon atoms, trifluoromethyl, benzyloxy or benzylthio, or represents thienyl, furyl, pyridyl or benzoxadiazolyl, or represents a heterocycle of the formula

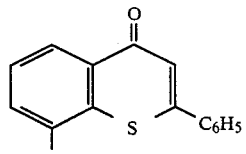

and n represents a number 2 to 8,
and their physiologically acceptable salts.

Physiologically acceptable salts are salts of the compounds according to the invention with inorganic or organic acids. These preferably include inorganic acids such as hydrohalic acids, preferably hydrochloric acid or hydrobromic acid, or sulphuric acid, or phosphoric acid, or organic carboxylic acids or sulphonic acids such as, for example, formic acid, acetic acid, propionic acid, maleic acid, fumaric acid, malic acid, citric acid, tartaric acid, lactic acid, benzoic acid, methanesulphonic acid, ethanesulphonic acid, benzenesulphonic acid, naphthalenedisulphonic acid or toluenesulphonic acid.

The compounds according to the invention consist in stereoisomeric forms which either are related as image and mirror image (enantiomers) or are not related as image and mirror image (diastereomers). The invention relates to both the antipodes and the racemic forms as well as to the mixtures of diastereomers. The racemic forms can be separated, in the same way as diastereomers, into the stereoisomerically pure constituents in a known manner (compare E. L. Eliel, Stereochemistry of Carbon Compounds, McGraw Hill, 1962).

The compounds according to the invention, of the general formula (I), are prepared by
[A] reaction of aldehydes of the general formula (II)

R-CHO (II)

in which R has the abovementioned meaning, and nitroacetone of the formula (III)

or their Knoevenagel condensation products (ylidene compounds) of the general formula (IV)

in which R has the abovementioned meaning, with enamines of the general formula (V)

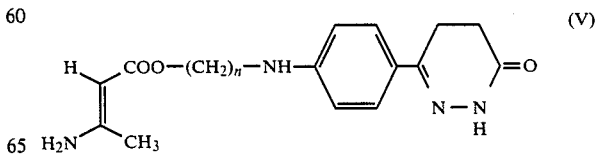

in which n has the abovementioned meaning, in the presence of inert solvents, or by

[B] reaction of aldehydes of the general formula (II) and ketones of the general formula (VI)

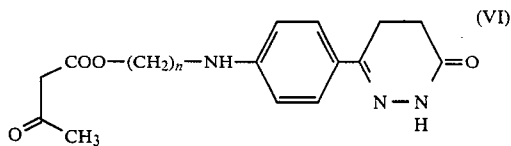 (VI)

in which n has the abovementioned meaning, or their Knoevenagel condensation products (ylidene compounds) of the general formula (VII)

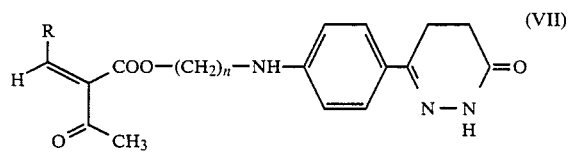 (VII)

in which R and n have the abovementioned meaning, with the enamine (nitroacetone/ammonia addition compound) of the formula (VIII)

 (VIII)

in the presence of inert solvents, or by

[C] reaction of 1,4-dihydropyridinecarboxylic esters of the general formula (IX)

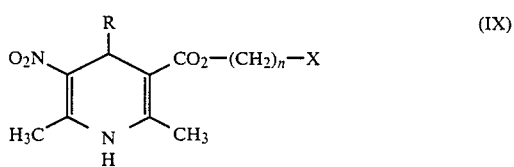 (IX)

in which
R and n have the abovementioned meaning, and
X represents a nucleofugic group such as, for example, bromide, iodide, mesylate, triflate or tosylate,
with the aniline of the formula (X)

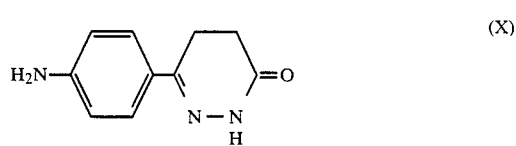 (X)

in the presence of an auxiliary base in an inert solvent, or by

[D] esterification of 1,4-dihydropyridinecarboxylic acids of the general formula (XI)

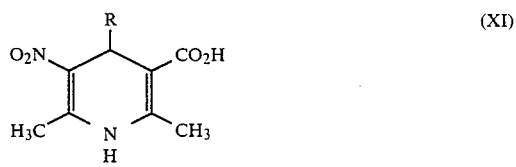 (XI)

in which R has the indicated meaning, by customary methods of esterification of carboxylic acids (for example via the carbonyl chloride or imidazolide or in the presence of dicyclohexylcarbodiimide) with the alcohol of the formula (XII)

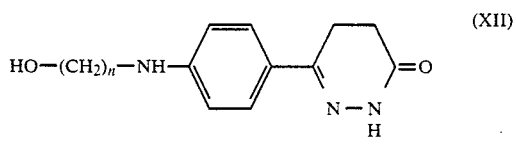 (XII)

in which n has the indicated meaning.

Depending on the nature of the starting compounds used, the process variants A to D can be illustrated by the following diagrams:

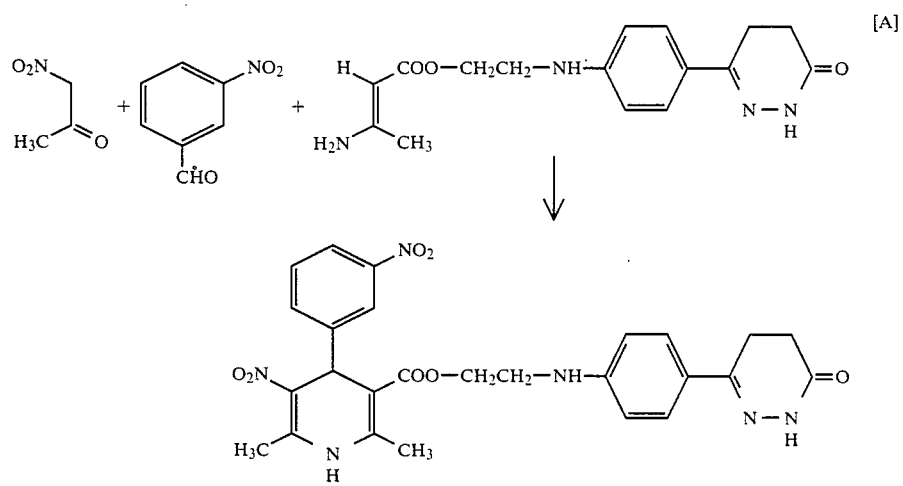

[A]

-continued
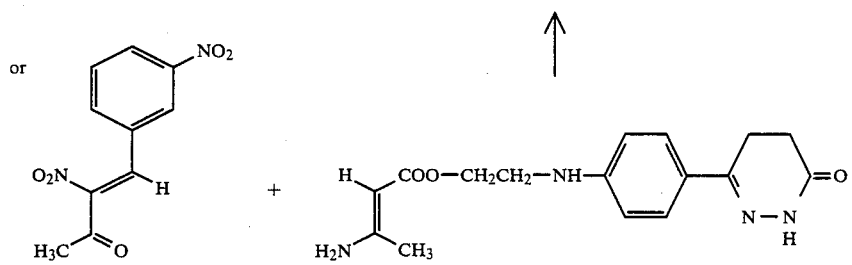
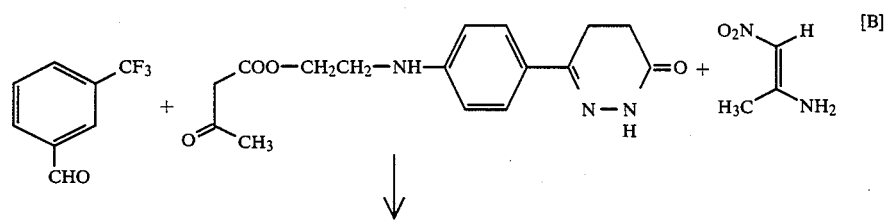
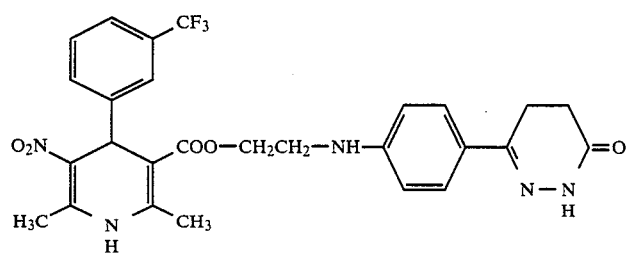
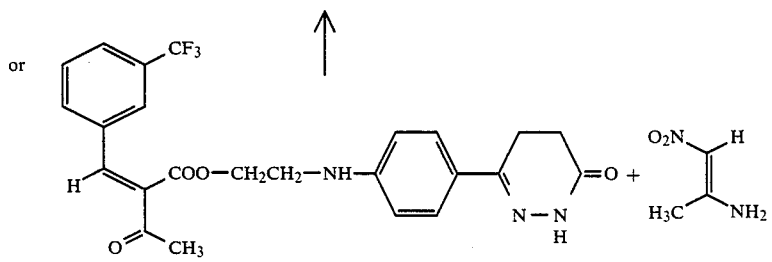
[B]
[C]
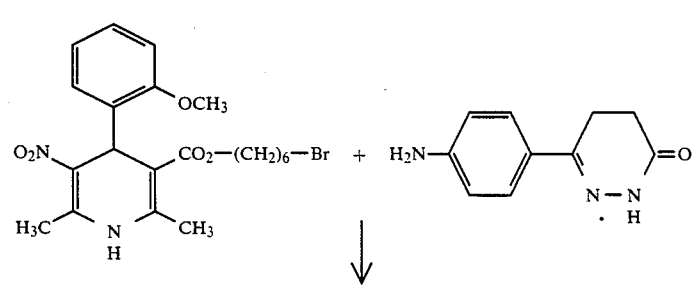
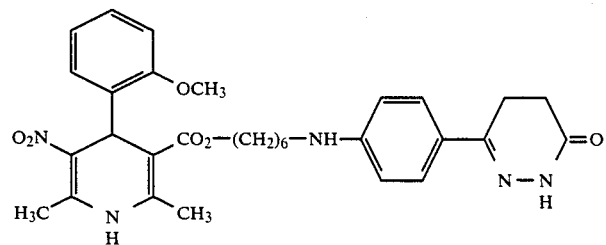

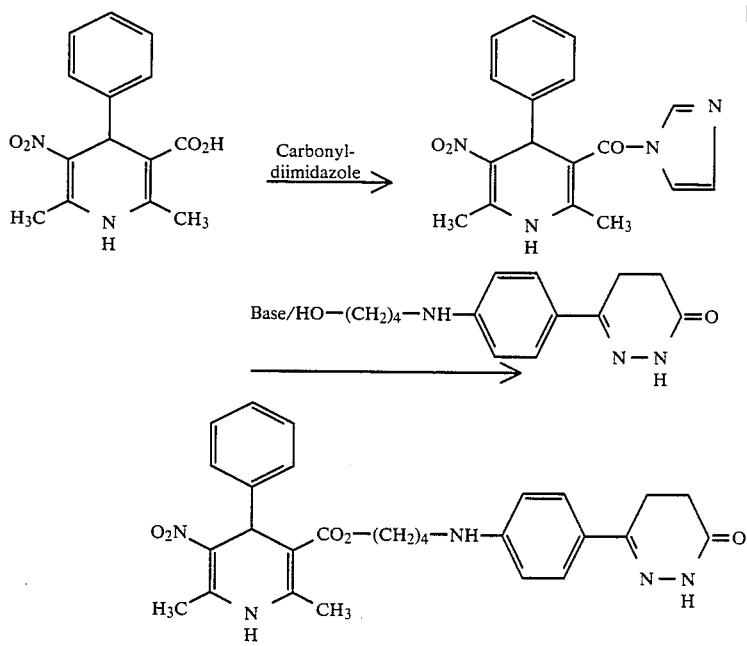

The aldehydes of the general formula (II) which are used as starting materials are known or can be prepared by known methods [E. Mosettig, Organic Reactions III, 218 (1954); Chemical Abstracts 59, 13929 (1963)].

The ketone of the formula (III) is known [N. Lewy, C. W. Scaife, J. Chem. Soc. (London) 1946, 1100; C. D. Hurd, M. E. Nilson J. Org. Chem. 20, 927 (1955); G. F. Field, W. J. Zally Synthesis 1979, 295]

The enamine (nitroacetone/ammonia addition compound) of the formula (VIII) is known [H. Boehme, K.-H. Weisel Arch. Pharm. 310, 30 (1977)].

The Knoevenagel condensation products of the general formula (IV) are known or can be prepared by known methods [A. Dornow, W. Sassenberg, Liebigs Ann. Chem. 602, 14 (1957)].

The ketones of the general formula (VI) are new. They are prepared by known methods [for example D. Borrmann, "Umsetzung von Diketen mit Alkoholen, Phenolen und Mercaptanen" (Reaction of diketene with alcohols, phenols and mercaptans) in Houben-Weyl's "Methoden der Organischen Chemie" (Methods of Organic Chemistry), vol. VII/4, 230 et seq. (1968)].

The enamines of the general formula (V) are new. They are prepared by known methods [compare, for example, A. C. Cope, J. Am. Chem. Soc. 67, 1047 (1945)].

The Knoevenagel condensation products (ylidene compounds) of the general formula (VII) are new. They are prepared by known methods [compare, for example, G. Jones, Organic Reactions XV, 204 (1967)].

The 1,4-dihydropyridinecarboxylic esters (IX) used as starting materials are known or can be prepared by known methods [compare German patent specification No. 3,206,671 and European patent specification No. 0,071,819].

The aniline (X) used as starting material is known or can be prepared by methods known from the literature [compare German Offenlegungsschriften Nos. 2,165,260; 2,847,237 and 2,401,665].

The carboxylic acids (XI) used as starting materials are known or can be prepared by methods known from the literature [compare German patent specification No. 2,206,671].

The amino alcohols of the formula (XII) used as starting materials are new and can be prepared by methods known from the literature [compare Organikum, page 191, VEB Deutscher Verlag der Wissenschaften Berlin 1963].

The solvents which can be used for processes A and B are water and all inert organic solvents which are not changed under the reaction conditions. These preferably include alcohols such as methanol, ethanol, propanol or isopropanol, or ethers such as diethyl ether, dioxane or tetrahydrofuran, or dimethylformamide, dimethyl sulphoxide, acetonitrile, glacial acetic acid, ethyl acetate, hexamethylphosphoric triamide or hydrocarbons such as benzene, toluene or xylene. It is equally possible to use mixtures of the said solvents.

The reaction temperatures for processes A and B can be varied within a relatively wide range. In general, a range from $+10°$ C. to $+200°$ C., preferably from $+20°$ C. to 140° C., in particular up to the boiling point of the solvent used, is employed.

The reactions can be carried out under atmospheric pressure as well as under elevated or reduced pressure. In general, atmospheric pressure is employed.

The ratio of the substances involved in the reaction when carrying out processes A and B according to the invention is arbitrary. In general, equimolar amounts of the reactants are employed. It has proved expedient in processes A and B to use nitroacetone or the nitroacetone/ammonia addition product in an excess of up to 20-fold, preferably up to 10-fold.

The procedure for process variant C according to the invention is derived from methods known from the literature for the alkylation of amines. This entails the activated alkyl ester IX being reacted with the aniline X in the presence of an auxiliary base. Examples of auxiliary bases which may be mentioned are: trialkylamines such as triethylamine, tributylamine, dimethylbenzylamine, methylhexylisopropylamine and DBU, DBN or sodium bistrimethylsilylamide.

The procedure for process variant D according to the invention is derived from methods known from the literature for the esterification of carboxylic acids. This entails the carboxylic acid first being converted into an activated form such as, for example, the acid chloride or the imidazolide, which is either isolated as such and reacted in a second reaction step or alkanolyzed in situ directly to give the compounds according to the invention. Examples of activating agents which may be mentioned apart from the inorganic halides such as thionyl chloride, phosphorus trichloride or phosphorus pentachloride are carbonyldiimidazole, carbodiimides such as dicyclohexylcarbodiimide or 1-cyclohexyl-3-[2-(N-methylmorpholino)ethyl]carbodiimide p-toluenesulphonate or N-hydroxyphthalimide or N-hydroxybenzotriazole in the presence of dicyclohexylcarbodiimide. Owing to their nature it is also possible to convert the 1,4-dihydropyridinemonocarboxylic acids into salts which can be reacted with substrates of the general formula (XIII)

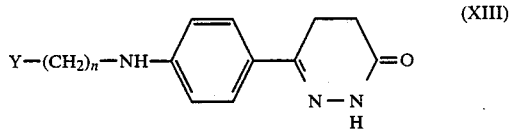

(XIII)

in which
n has the indicated meaning, and
Y represents a nucleofugic group such as, for example, iodide or tosylate,
to give the compounds according to the invention.

Suitable diluents are all inert organic solvents. These preferably include ethers such as dioxane, tetrahydrofuran, glycol monomethyl ether or glycol dimethyl ether, halogenated hydrocarbons, such as dichloromethane or trichloromethane, dimethylformamide, dimethyl sulphoxide, acetonitrile, pyridine and hexamethylphosphoric triamide. If the activated intermediates of the 1,4-dihydro monocarboxylic acids are isolated it is also possible to use the alcohol of the formula (XII) alone as diluent.

The rate of the alkanolysis is expediently increased by addition of catalytic or equimolar amounts of a basic auxiliary.

The ratio of the substances involved in the reaction when carrying out processes C and D according to the invention is arbitrary. In general, equimolar amounts of the reactants are employed.

The reaction temperatures can be varied within a relatively wide range. In general, between +10° C. and +200° C., in particular between +20° C. and +150° C., but preferably at the boiling point of the particular solvent, is employed.

The reaction can be carried out under atmospheric pressure as well as under elevated pressure. In general, atmospheric pressure is employed.

The compounds according to the invention exhibit a valuable spectrum of pharmacological actions which could not have been predicted. They influence the myocardial contractility and the tone of smooth muscle. Hence they can be used in medicaments for influencing pathologically changed blood pressure, as coronary therapeutics and for the treatment of heart failure. In addition, they can be used for the treatment of cardiac arrhythmias, for lowering the blood sugar, for reducing the swelling of mucous membranes and for influencing the salt and fluid balance.

The cardiovascular effects have been found on the isolated, perfused guinea pig heart.

Hearts from guinea pigs weighing 250 to 350 g are used for this. The animals are killed by a blow to the head, the thorax is opened, and a metal cannula is tied into the exposed aorta. The heart and the lungs are removed from the thorax and attached via an aortic cannula to the perfusion apparatus while perfusion continues. The lungs are detached at the lung roots. The perfusion medium used is a Krebs-Henseleit solution (1) (118.5 mmol/l NaCl, 4.75 mmol/l KCl, 1.19 mmol/l $KH_2PO_4$, 1.19 mmol/l $MgSO_4$, 25 mmol/l $NaHCO_3$, 0.013 mmol/l $Na_2EDTA$), whose $CaCl_2$ content is 1.2 mmol/l. 10 mmol/l glucose are added as energy-supplying substrate. Before the perfusion the solution is filtered to remove particles. Carbogen (95% $O_2$, 5% $CO_2$) is passed through the solution to maintain the pH at 7.4. The hearts are perfused at a constant flow rate (10 ml/min) at 32° C. using a peristaltic pump.

To measure the functioning of the heart, a liquid-filled latex ballon which is connected via a liquid column to a pressure transducer is introduced through the left atrium into the left ventricle, and the isovolumetric contractions are recorded on a fast-response pen recorder (Opie, L., J. Physiol. 180 (1965), 529–541). The perfusion pressure is recorded by means of a pressure transducer which is connected to the perfusion system upstream of the heart. Under these conditions a decrease in the perfusion pressure indicates coronary dilatation, and a rise or fall in the amplitude of contraction of the left ventricle indicates an increase or decrease in cardiac contractility. The compounds according to the invention are infused into the perfusion medium at suitable dilutions shortly upstream of the isolated heart.

The following values show, by way of example, the effect of the compounds according to the invention on the isolated, perfused guinea pig heart, expressed as the percentage difference from the initial value, which is set equal to 100%.

| Example No. | Concentration (g/l) | % change in contractility | % change in perfusion pressure |
|---|---|---|---|
| 5 | $10^{-6}$ | +3% | −17% |
| 7 | $10^{-6}$ | +9% | −17% |
| 8 | $10^{-6}$ | +16% | −27% |
| 9 | $10^{-6}$ | +40% | −26% |

In addition, the substances of the general formula (I) according to the invention act as inhibitors/stimulators of enzymatic reactions in arachidonic acid metabolism. Substances of this type are suitable for the prevention and treatment of disorders of the airways such as emphysema, shock lung, pulmonary hypertension, oedema, thrombosis and thromboembolism, ischaemia (disturbances of peripheral, coronary and cerebral blood flow), myocardial and cerebral infarcts, cardiac arrhythmias, angina pectoris, hypertension and arteriosclerosis. The substances according to the invention act preferentially to inhibit platelet aggregation.

Blood from healthy subjects of both sexes was used to determine the action inhibiting platelet aggregation. One part of 3.8% strength aqueous sodium citrate solution was mixed as anticoagulant with 9 parts of blood. Platelet-rich citrated plasma (PRP) (Jügens/Beller, Klinische Methoden der Blutgerinnungsanalyse (Clinical Methods in Clotting Analysis); Thieme Verlag, Stuttgart, 1959) was obtained from this by centrifugation.

For these investigations, 0.8 ml of PRP and 0.1 ml of the active compound solution were preincubated at 37° C. in a waterbath. The platelet aggregation was then determined by the turbidometric method (Born, G. V. R., J. Physiol. (London), 162, 67, 1962) in an aggregometer at 37° C. (Therapeutische Berichte 47, 80–86, 1975). For this purpose, 0.1 ml of collagen, an agent which initiates aggregation, was added to the preincubated sample. The change in the optical density in the sample of PRP was recorded for a period of 4 minutes, and the excursion after 4 minutes was determined. For this purpose, the percentage inhibition compared with the control is calculated.

The minimum effective concentration is reported as being the concentration which shows an inhibition of at least 25%. At and above 3 μg/ml the inventive substances inhibit collagen-induced platelet aggregation.

The new active compounds can be converted in a known manner into the customary formulations, such as tablets, coated tablets, pills, granules, aerosols, syrups, emulsions, suspensions and solutions, using inert, non-toxic pharmaceutically suitable excipients or solvents. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut/sesame oil), alcohols (for example: ethyl alcohol and glycerol), excipients such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters, polyoxyethylene fatty alcohols, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the excipients mentioned, additives such as sodium citrate, calcium carbonate and dicalcium phosphate, together with various additional substances, such as starch, preferably potato starch, gelatin and the like. Furthermore, lubricants such as magnesium stearate, sodium lauryl sulphate and talc can also be used when making tablets. In the case of aqueous suspensions, the active compounds can be mixed with various flavor-improving agents or colorants in addition to the abovementioned auxiliaries.

In the case of parental administration, solutions of the active compound, employing suitable liquid vehicles, can be used.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 to 10 mg/kg, of body weight.

Nevertheless, it can at times be necessary to deviate from the amounts mentioned, and in particular to do so as a function of the body weight or of the nature of the mode of administration, of the individual behavior towards the medicament, of the nature of its formulation and the time or interval over which administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day.

Preparation examples

Example 1

N-(6-Hydroxyhexyl)-4-(6-oxo-1,4,5,6-tetrahydro-3-pyridazinyl)aniline

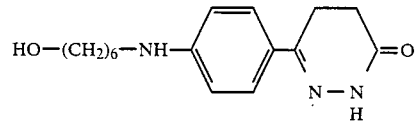

1.65 g of sodium hydride are introduced into 50 ml of dimethylformamide. 9.45 g of 4-(6-oxo-1,4,5,6-tetrahydro-3-pyridazinyl)aniline are added in portions. A solution of 5.9 g of 6-bromohexyl tetrahydropyranyl ether is added dropwise to this mixture. The mixture is stirred at room temperature for 2 hours and then poured onto water. The precipitate is filtered off with suction and washed with water, then dissolved in methanol and heated to reflux, with the addition of 2 g of ion exchanger with sulphonic acid groups, for 8 hours. The crude residue from evaporation is, after removal of the ion exchanger by filtration, further processed.

Example 2

6-[4-(6-Oxo-1,4,5,6-tetrahydro-3-pyridazinyl)anilino]-hexyl acetoacetate

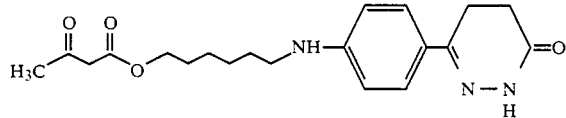

12.8 g of the product from Example 1 in 250 ml of tetrahydrofuran are heated to reflux. 18 g of diketene in 20 ml of tetrahydrofuran are added dropwise. The mixture is then heated to reflux for 2 hours, the solvent is removed by distillation in vacuo, and the residue is crystallized from a little isopropanol.

Melting point: 125° C.

Yield: 10.2 g (62% of theory).

Example 3

6-[4-(6-Oxo-1,4,5,6-tetrahydro-3-pyridazinyl)anilino]-hexyl 3-aminocrotonate

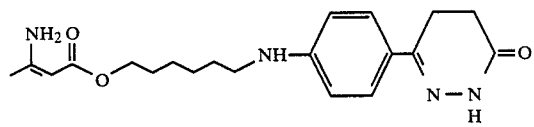

5.5 g of the acetoacetate from Example 2 in 150 ml of tetrahydrofuran and 0.2 g of p-toluenesulphonic acid are heated to reflux. Ammonia is passed in for 6 hours during this. After cooling, the mixture is concentrated, and the residue is recrystallized from isopropanol.

Melting point: 4.8 g (87% of theory).

Example 4

3-[4-(6-Oxo-1,4,5,6-tetrahydro-3-pyridazinyl)anilino]-propyl 3-aminocrotonate

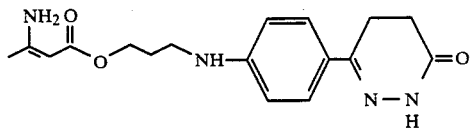

The title compound is prepared in analogy to Example 3 from N-(3-hydroxypropyl)-4-(6-oxo-1,4,5,6-tetrahydro-3-pyridazinyl)aniline.

Example 5

3-[4-(6-Oxo-1,4,5,6-tetrahydro-3-pyridazinyl)anilino]-propyl 3-oxo-1-(2-trifluoromethylphenyl)but-1-ene-2-carboxylate

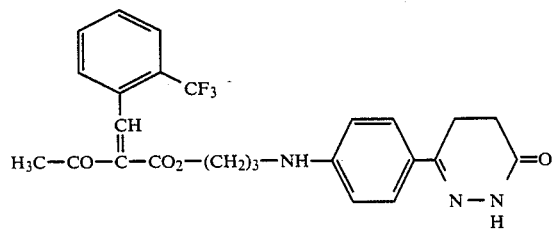

30 mmol of 1-butyliminomethyl-2-trifluoromethyl-benzene and 30 mmol of 3-[4-(6-oxo-1,4,5,6-tetrahydro-3-pyridazinyl)anilino]propyl acetoacetate in 25 ml of acetic anhydride are stirred at room temperature for 24 hours, then the mixture is poured onto water, the aqueous phase is decanted off, and the residue is digested with a little isopropanol.

Yield: 68% of theory.
Melting point: 136° C.

Example 6

6-[4-(6-Oxo-1,4,5,6-tetrahydro-3-pyridazinyl)anilino]-hexyl 1,4-dihydro-2,6-dimethyl-5-nitro-4-(2-trifluoromethylphenyl)pyridine-3-carboxylate

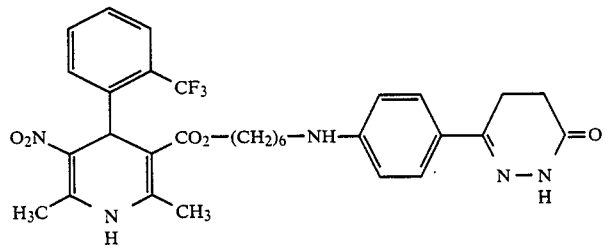

Process A 10 mmol of 2-nitro-1-(2-trifluoromethylphenyl)but-1-en-3-one and 10 mmol of 6-[4-(6-oxo-1,4,5,6-tetrahydro-3-pyridazinyl)anilino]hexyl 3-aminocrotonate in 30 ml of isopropanol are heated to reflux for 4 hours. The compound crystallizes out on cooling and is recrystallized from isopropanol.

Yield: 4.1 g (80% of theory).
Melting point: 140° C. (decomposition).

Process C 10 mmol of 6-bromohexyl 1,4-dihydro-2,6-dimethyl-5-nitro-4-(2-trifluoromethylphenyl)pyridine-3-carboxylate and 10 mmol of 4-(6-oxo-1,4,5,6-tetrahydro-3-pyridazinyl)aniline and 5mmol of DBN in isopropanol are heated to reflux for 10 hours. The mixture is cooled and then filtered, and the residue from evaporation is chromatographed on silica gel using chloroform and 10% methanol.

Melting point: 140° C. (decomposition).
Yield: 32% theory.

Example 7 (variant B with condensation product)

6-[4-6-Oxo-1,4,5,6-tetrahydro-3-pyridazinyl)anilino]-propyl 1,4-dihydro-2,6-dimethyl-5-nitro-4-(2-trifluoromethylphenyl)pyridine-3-carboxylate

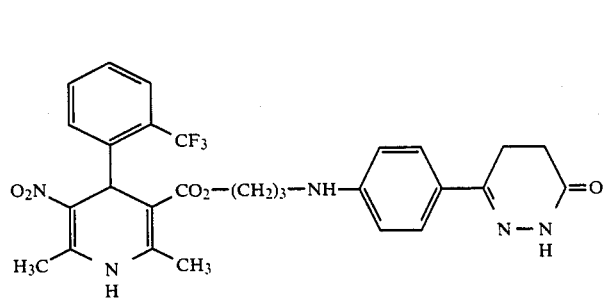

30 mmol of ammonia/nitroacetone addition product are added in portions to 10 mmol of benzylidene compound from Example 5 in 30 ml of isopropanol at 60° C. The mixture is then stirred for 4 hours. The product is purified by column chromatography on silica gel using chloroform plus 10% methanol.

Yield: 26% of theory.
Melting point: 182° C.

Example 8 (variant A with condensation product)

3-[4-(6-Oxo-1,4,5,6-tetrahydro-3-pyridazinyl)anilino]-propyl 1,4-dihydro-2,6-dimethyl-5-nitro-4-(3-nitrophenyl)pyridine-3-carboxylate

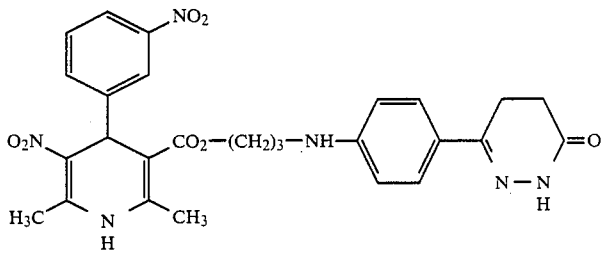

10 mmol of 2-nitro-1-(3-nitrophenyl)but-1-en-3-one and 10 mmol of 3-[4-(6-oxo-1,4,5,6-tetrahydro-3-pyridazinyl)anilino]propyl 3-aminocrotonate in 30 ml of isopropanol are heated at 60° C. for 6 hours. After the solvent has been removed by distillation, the residue is chromatographed on silica gel using chloroform plus 10% methanol.

Yield: 32% of theory.
Melting point: 166° C.

Example 9 (variant A with condensation product)

3-[4-(6-Oxo-1,4,5,6-tetrahydro-3-pyridazinyl)anilino]-propyl 4-(2-benzyloxyphenyl)-1,4-dihydro-2,6-dimethyl-5-nitropyridine-3-carboxylate

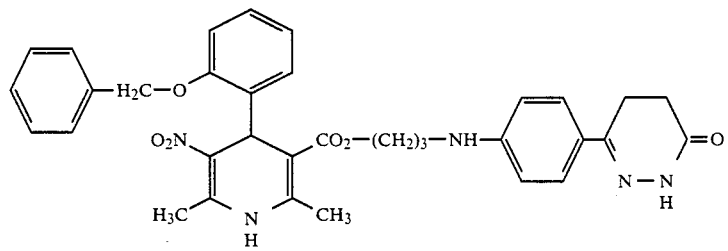

The title compound is prepared in analogy to Example 8 from 1-(2-benzyloxyphenyl)-2-nitrobut-1-en-3-one and 3-[4-(6-oxo-1,4,5,6-tetrahydro-3-pyridazinyl)anilino]propyl 3-aminocrotonate.

Yield: 29% of theory.
Melting point: resin.

Example 10 (variant A with condensation product)

6-Bromohexyl 1,4-dihydro-2,6-dimethyl-5-nitro-4-(2-trifluoromethylphenyl)pyridine-3-carboxylate

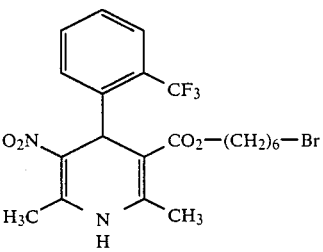

50 mmol of 2-nitro-1-(2-trifluoromethylphenyl)but-1-en-3-one and 50 mmol of 5-bromohexyl 3-aminocrotonate in isopropanol are heated at 60° C. for 6 hours. The product crystallizes after part of the solvent had been evaporated off.

Melting point: 117° C.
Yield: 42% of theory.

Example 11 (variant A)

4-[4-(6-Oxo-1,4,5,6-tetrahydro-3-pyridazinyl)anilino]-butyl 4-(2-chlorophenyl)-1,4-dihydro-2,6-dimethyl-5-nitropyridine-3-carboxylate

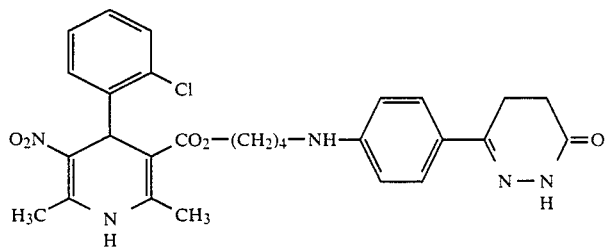

The title compound is obtained in analogy to Example 5 from 1-(2-chlorophenyl)-2-nitrobut-1-en-3-one and 4-[4-(6-oxo-1,4,5,6-tetrahydro-3-pyridazinyl)anilino]butyl 3-aminocrotonate.

Melting point: 143° C. (decomposition).

Example 12 (variant A)

6-[4-(6-Oxo-1,4,5,6-tetrahydro-3-pyridazinyl)anilino]hexyl 1,4-dihydro-2,6-dimethyl-4-(2-methoxyphenyl)-5-nitropyridine-3-carboxylate

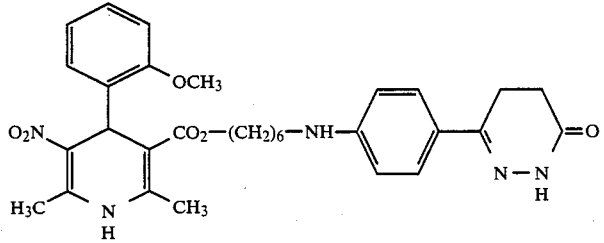

50 mmol of nitroacetone/ammonia addition compound are added in portions to 20 mmol of 2-methoxybenzaldehyde and 20 mmol of 6-[4-(6-oxo-1,4,5,6-tetrahydro-3-pyridazinyl)anilino]hexyl 3-aminocrotonate in 50 ml of isopropanol at 40° C. The mixture is then stirred for 4 h and evaporated. The residue is chromatographed on silica gel using chloroform plus 10% methanol.

Yield: 26% of theory.
Melting point: resin.

It will be understood that the specification and examples are illustrative but not limitative of the present invention and that other embodiments within the spirit and scope of the invention will suggest themselves to those skilled in the art.

I claim:
1. A nitrodihydropyridine of the formula

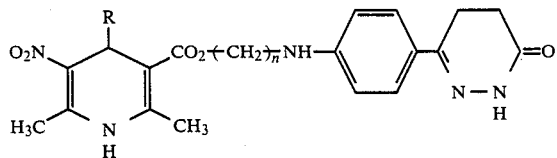

in which
R represents phenyl or naphthyl, each of which can be substituted up to 3 times, identically or differently, by fluorine, chlorine, bromine, nitro, cyano, alkyl, alkoxy, alkylthio, each having up to 4 carbon atoms, trifluoromethyl, trifluoromethoxy or trifluoromethylthio, or benzyloxy or benzylthio, each of which is optionally substituted by nitro, fluorine, chlorine, bromine, trifluoromethyl, methyl or methoxy, or represents a heterocycle which is optionally substituted by methyl, fluorine, chlorine, bromine or phenyl and is from the group consisting of thienyl, furyl, pyridyl, pyrimidyl, quinolyl, benzoxadiazolyl or thiochromenyl, and
n represents a number from 1 to 10,
or a physiologically acceptable salt thereof.

2. A compound or salt according to claim 1, in which
R represents phenyl which can be substituted up to twice, identically or differently, by fluorine, chlorine, nitro, alkoxy having up to 4 carbon atoms, trifluoromethyl, benzyloxy or benzylthio, and
n represents a number from 2 to 6.

3. A compound or salt according to claim 1, in which
R represents phenyl which can be substituted up to twice, identically or differently, by fluorine, chlorine, nitro, cyano, alkyl, alkoxy, each having up to 4 carbon atoms, trifluoromethyl, benzyloxy or benzylthio, or represents thienyl, furyl, pyridyl or benzoxadiazolyl, or represents a heterocycle of the formula

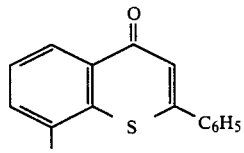

and n represents a number from 2 to 8.

4. A compound according to claim 1, wherein such compound is 6-[4-(6-oxo-1,4,5,6-tetrahydro-3-pyridazinyl)anilino]hexyl 1,4-dihydro-2,6-dimethyl-5-nitro-4-(2-trifluoromethylphenyl)pyridine-3-carboxylate of the formula

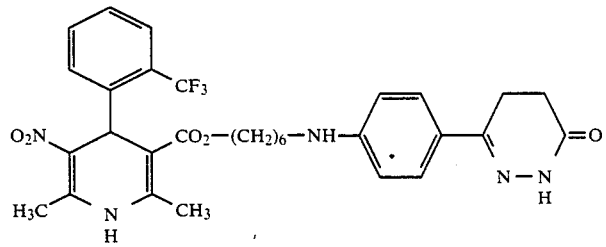

or a physiologically acceptable salt thereof.

5. A compound according to claim 1, wherein such compound is 3-[4-(6-oxo-1,4,5,6-tetrahydro-3-pyridazinyl)anilino]propyl 1,4-dihydro-2,6-dimethyl-5-nitro-4-(3-nitrophenyl)pyridine-3-carboxylate of the formula

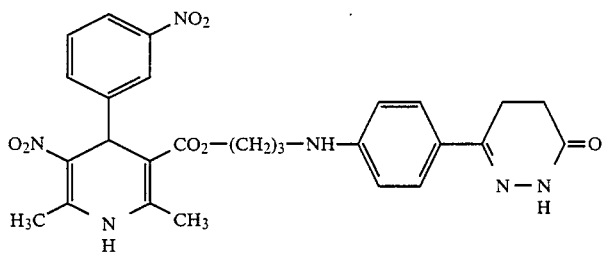

or a physiologically acceptable salt thereof.

6. A compound according to claim 1, wherein such compound is 4-[4-(6-oxo-1,4,5,6-tetrahydro-3-pyridazinyl)anilino]butyl 4-(2-chlorophenyl)-1,4-dihydro-2,6-dimethyl-5-nitropyridine-3-carboxylate of the formula

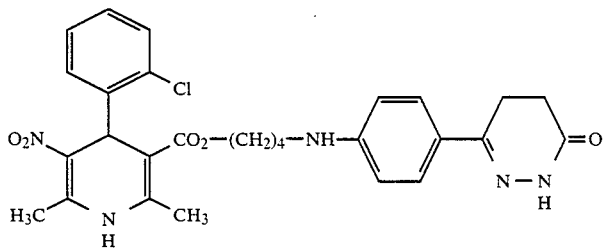

or a physiologically acceptable salt thereof.

7. A cardioactive composition comprising a cardioactive effective amount of a compound or salt according to claim 1 and a pharmaceutically acceptable diluent.

8. A unit dose of a composition according to claim 7 in the form of a tablet, capsule or ampule.

9. A method of modifying the coronary activity of a patient in need thereof which comprises administering to such patient a cardioactive effective amount of a compound or salt according to claim 1.

10. The method according to claim 9, wherein such compound is

6-[4-(6-oxo-1,4,5,6-tetrahydro-3-pyridazinyl)anilino]hexyl 1,4-dihydro-2,6-dimethyl-5-nitro-4-(2-trifluoromethylphenyl)-pyridine-3-carboxylate, 3-[4-(6-oxo-1,4,5,6-tetrahydro-3-pyridazinyl)anilino]propyl 1,4-dihydro-2,6-dimethyl-5-nitro-4-(3-nitrophenyl)pyridine-3-carboxylate, or 4-6-oxo-1,4,5,6-tetrahydro-3-pyridazinyl)anilino]butyl 4-(2-chlorophenyl)-1,4-dihydro-2,6-dimethyl]-5-nitropyridine-3-carboxylate.

* * * * *

UNITED STATES PATENT AND TRADEMARK OFFICE
CERTIFICATE OF CORRECTION

PATENT NO. : 4,898,865

DATED : February 6, 1990

INVENTOR(S) : Franckowiak et al.

It is certified that error appears in the above-identified patent and that said Letters Patent is hereby corrected as shown below:

Col. 20, claim 10    Delete " 4-6-oxo " and substitute -- 4-[4-(6-oxo --
line 9

Col. 20, claim 10    After " dimethyl " delete " ] "
line 10

Signed and Sealed this

Sixth Day of July, 1993

Attest:

MICHAEL K. KIRK

*Attesting Officer*    *Acting Commissioner of Patents and Trademarks*